US010617569B2

(12) United States Patent
Bonn (10) Patent No.: US 10,617,569 B2
(45) Date of Patent: Apr. 14, 2020

(54) SYSTEM FOR WOUND TREATMENT USING A SERUM (71) Applicant: 3M INNOVATIVE PROPERTIES COMPANY, St. Paul, MN (US)

(72) Inventor: Florian Bonn, Leverkusen (DE)

(73) Assignee: 3M Innovative Properties Company, Saint Paul, MN (US)

( * ) Notice: Subject to any disclaimer, the term of this patent is extended or adjusted under 35 U.S.C. 154(b) by 398 days.

(21) Appl. No.: 15/571,407

(22) PCT Filed: May 10, 2016

(86) PCT No.: PCT/IB2016/052660
§ 371 (c)(1),
(2) Date: Nov. 2, 2017

(87) PCT Pub. No.: WO2016/181301
PCT Pub. Date: Nov. 17, 2016

(65) Prior Publication Data
US 2018/0303676 A1 Oct. 25, 2018

(30) Foreign Application Priority Data
May 11, 2015 (EP) .................................... 15167089

(51) Int. Cl.
*A61F 13/00* (2006.01)
*B01D 63/02* (2006.01)
(Continued)

(52) U.S. Cl.
CPC .......... *A61F 13/00068* (2013.01); *A61J 1/10* (2013.01); *A61M 1/0218* (2014.02);
(Continued)

(58) Field of Classification Search
CPC ........ A61M 2202/0423; A61M 1/0218; A61M 1/0259; A61M 1/0281; A61K 35/16; A61F 2013/0017; A61J 1/10
See application file for complete search history.

(56) References Cited

U.S. PATENT DOCUMENTS 4,639,243 A  1/1987 Schmidt
4,744,240 A  5/1988 Reichelt
(Continued)

FOREIGN PATENT DOCUMENTS

DE  28 33 493  2/1980
DE  38 39 567  6/1990
(Continued)

OTHER PUBLICATIONS

Brune, T., et al., "Quality, Stability, and Safety Data of Packed Red Cells and Plasma Processed by Gravity Separation Using a New Fully Integrated Hollow-Fibre Filter Device", *Advances in Hematology*, Bd. 45, Nr. 3, 1 Jan. 1, 2009 XP055223360.
(Continued)

*Primary Examiner* — Susan S Su
(74) *Attorney, Agent, or Firm* — 3M Innovative Properties Company; Trisha D. Adamson (57) ABSTRACT A system for wound treatment using a serum, comprising a device for recovering serum from whole blood, comprising:
a blood bag for the reception and coagulation of whole blood, which has an outlet for discharging the serum-containing fluid from the blood bag and a barrier in the region of the outlet for retaining the coagulum,
a filter module which is fluidically connected to the blood bag and comprises a housing and an interior, in which a semi-permeable membrane is arranged, said membrane dividing the interior into a retentate space and a permeate space and separating the fluid discharged from the blood bag into a permeate comprising the
(Continued)

serum and into a retentate in which any particulate components contained in the fluid remain.

The system for wound treatment further comprises a wound care system with a capillary membrane system for dispensing the serum to a wound. The capillary membrane system is connected to at least one supply line, which for its part is connected to the permeate outlet of the filter module.

15 Claims, 3 Drawing Sheets

(51) Int. Cl.
*A61M 1/02* (2006.01)
*A61J 1/10* (2006.01)
*B01D 61/14* (2006.01)
*A61K 35/16* (2015.01)

(52) U.S. Cl.
CPC ......... *A61M 1/0281* (2013.01); *B01D 61/147* (2013.01); *B01D 63/02* (2013.01); *A61F 2013/0017* (2013.01); *A61K 35/16* (2013.01); *A61M 2202/0423* (2013.01)

(56) References Cited

U.S. PATENT DOCUMENTS

| | | | |
|---|---|---|---|
| 4,898,573 A | 2/1990 | Takenale | |
| 4,976,859 A | 12/1990 | Wechs | |
| 5,141,031 A | 8/1992 | Baurmeister | |
| 5,620,790 A | 4/1997 | Holzki | |
| 6,165,363 A | 12/2000 | Oishi | |
| 6,645,388 B2 | 11/2003 | Sheikh-Ali | |
| 8,419,705 B2* | 4/2013 | Omori | A61M 1/3693 604/403 |
| 8,721,617 B2* | 5/2014 | Omori | A61F 5/44 210/787 |
| 9,321,013 B2 | 4/2016 | Bornemann | |
| 2002/0147098 A1* | 10/2002 | Dolecek | A61M 1/3696 494/37 |
| 2002/0183678 A1* | 12/2002 | Heim | A61M 1/3496 604/6.04 |
| 2005/0015064 A1 | 1/2005 | Gerlach | |
| 2005/0107868 A1 | 5/2005 | Nakayama | |
| 2005/0142208 A1* | 6/2005 | Yoo | A61K 35/16 424/529 |
| 2006/0251622 A1* | 11/2006 | Suzuki | A61M 1/0209 424/93.2 |
| 2008/0197072 A1 | 8/2008 | Ansorge | |
| 2009/0196855 A1 | 8/2009 | Bornemann | |
| 2009/0261038 A1 | 10/2009 | Heim | |
| 2010/0120150 A1* | 5/2010 | Suzuki | A61K 35/16 435/404 |
| 2010/0211041 A1* | 8/2010 | Omori | A61M 1/029 604/403 |
| 2010/0224553 A1 | 9/2010 | Ruetering | |
| 2011/0213319 A1 | 9/2011 | Blott | |
| 2012/0171658 A1 | 7/2012 | Bein | |
| 2012/0215193 A1* | 8/2012 | Siniaguine | A61F 13/0206 604/368 |
| 2013/0046223 A1 | 2/2013 | Schrammel | |
| 2013/0058906 A1* | 3/2013 | Turzi | A61M 5/19 424/93.7 |
| 2014/0227241 A1* | 8/2014 | Lacza | A61L 27/3616 424/93.72 |
| 2015/0015064 A1 | 1/2015 | Gerlach | |
| 2015/0165093 A1* | 6/2015 | Campbell | A61L 27/3616 424/530 |
| 2016/0287446 A1* | 10/2016 | Meixner | A61F 13/00025 |
| 2017/0035809 A1* | 2/2017 | Lacza | A61L 27/3616 |

FOREIGN PATENT DOCUMENTS

| | | |
|---|---|---|
| DE | 43 08 850 | 9/1994 |
| DE | 29 516 471 | 1/1996 |
| EP | 0 266 683 | 5/1988 |
| EP | 0 299 381 | 1/1989 |
| EP | 0 882 494 | 12/1998 |
| EP | 1 230 940 | 8/2002 |
| EP | 2 174 676 | 4/2010 |
| WO | WO 2000/043114 | 1/2000 |
| WO | WO 2000/062840 | 10/2000 |
| WO | WO 2002/013888 | 2/2002 |
| WO | WO 2006/131290 | 12/2006 |
| WO | WO 2007/128488 | 11/2007 |
| WO | WO 2009/134967 | 11/2009 |
| WO | WO 2011/157822 | 12/2011 |
| WO | WO 2012/139896 | 10/2012 |
| WO | WO 2014/207140 | 12/2014 |
| WO | WO 2015/031654 | 3/2015 |
| WO | WO 2015/071279 | 5/2015 |
| WO | WO 2015/071280 | 5/2015 |

OTHER PUBLICATIONS

HIMA-Vorschrift No. 3, vol. 4, 1982 (Health Industry Manufacturers Association) beschrieben.

"Leukozytendepletion" Retrieved May 10, 2017 http://flexikon.doccheck.com/de/Leukozytendepletion.

"Ultrafiltration" Retrieved May 4, 2017 https://de.wikipedia.org/wiki/Ultrafiltration.

"Wasserwert" Retrieved May 4, 2017 http://de.wikipedia.org/wiki/Wasserwert.

Zeman, Zydney, Microfiltration and Ultrafiltration Principles and Applications, pp. 14-17 (1996).

* cited by examiner

SYSTEM FOR WOUND TREATMENT USING A SERUM

CROSS REFERENCE TO RELATED APPLICATIONS

This application is a national stage filing under 35 U.S.C. 371 of PCT/IB2016/052660, filed May 10, 2016, which claims the benefit of EP Patent Application No. 15167089.0, filed May 11, 2015, the disclosures of which are incorporated by reference in their entirety herein.

The invention relates to a wound care system for introduction into a wound or for application to a skin wound and under a wound dressing, comprising a capillary membrane system having a planar configuration, wherein the capillary membrane system having a planar configuration is connected to at least one supply line so that fluids, media, gases and/or other substances can be passed through the supply line and the capillary membrane system.

Modern wound care pursues the goal of creating a moist wound environment in wound care that promotes ongoing processes during healing. Depending upon the healing phase, modern active wound dressings must therefore be able to keep the wound moist, to provide for an improved fluid/material exchange, for the introduction of factors/medicines into the wound, and/or for an improved removal of fluids, secretions and/or materials from the wound. Applications include the use of such wound dressing systems in a soft-tissue wound, in an abdominal wound and on a skin wound A method and a device for removing secretions or exudate from wounds is commercially known as the V.A.C.® Therapy System (KCI Co., USA). In this system, an alternating introduction of fluid into the wound and a subsequent, therefore also alternating and thus non-continuous, carrying of fluid from the wound is ensured. A foamed material introduced into the wound, which exerts forces onto the wound given negative pressure, should promote wound healing in this system.

A capillary membrane system for wound treatment is described in DE 10 2006 042 732, in which the wound is perfused and supplied via a hollow-fiber membrane device made from up to 1000 hollow fibers having at least one common supply and at least one common discharge, in the sense of flowing through a capillary bed, and perfusion of an antibiotic as well as of growth factors should be enabled. A uniform substance distribution under continuous perfusion and under the creation of a moderate negative pressure is thereby possible. DE 10 2006 042 732 states that additional capillary systems are advantageous for optimal supply and drainage.

Even though progress in wound management was already achievable via the capillary membrane system described in DE 10 2006 042 732, there is need of a simple and efficient wound care system, with which, first, processes necessary in wound management, such as rinsing and disinfecting, can be performed without removing the dressing; which enable nourishment, electrolytic exchange and/or detoxification, or also supplying of growth factors or a supply of antibiotics, as needed; and that permit simple and safe handling.

Wound treatments are also increasingly being worked on in which autologous or heterologous serum is supplied to the wound in order to accelerate the healing process. Wound treatment using serum can take place continuously as well as discontinuously. The ideal application depends upon the wound and must be individually determined for the patient to be treated.

Therefore, there is a desire for a wound care system that enables the targeted introduction of blood serum into the wound to be treated. It is therefore the object of the present invention to provide a system of this sort for wound treatment.

The object is achieved by a system for wound treatment using serum that comprises a device for recovering serum from whole blood, wherein the device for recovering serum from whole blood includes:
  a blood bag for receiving whole blood and for coagulating the whole blood into a solid fraction containing the cell components of the blood and a fluid contained in a serum, wherein the blood bag has an outlet for discharging the fluid from the blood bag and a barrier in the region of the outlet that is suitable for retaining at least a majority of the solid fraction,
  a filter module that is in fluidic connection with the blood bag via the blood bag outlet,
    wherein the filter module has a housing with an interior space and an inner wall that delimits the interior space, in which a semipermeable membrane is arranged that separates the interior space into a retentate space and a permeate space,
    wherein the semipermeable membrane enables a separation of the fluid discharged from the blood bag into a permeate that contains the serum and into a retentate, in which any particulate components contained in the blood remain, and
    wherein the filter module has an inlet device for introducing the fluid discharged from the blood bag into the retentate space, a retentate outlet for discharging the retentate from the retentate space, and a permeate outlet for discharging the permeate from the permeate space, and
  wherein the system for wound treatment additionally comprises a wound care system for deploying the permeate at a wound, which wound care system has a first capillary membrane system with a planar configuration, wherein the first capillary membrane system is connected to at least one supply line so that fluids can be conducted through the supply line and the first capillary membrane system and be delivered to the wound, and wherein the permeate outlet is connected to the first capillary membrane system via the permeate line that includes the at least one supply line of the first capillary membrane system.

Using such a system for wound treatment, it is possible to directly supply serum to a wound, wherein a simultaneous, almost homogeneous distribution of serum in the wound is possible. The configuration of the wound care system thus simultaneously allows a safe and simple handling. In application, the wound care system can also be inserted into the wound and, for example, be covered using a semi-occlusive, transparent film in order to protect the wound from drying out or from infection.

The first capillary membrane system is fluidically connected to the device for recovering serum via the at least one supply line of the first capillary membrane system. The blood serum created in the filter module can thus be applied into the wound via the first capillary membrane system.

In principle, devices such as those used in particular for plasma separation, meaning for recovering blood plasma and erythrocyte concentrates under the effect of gravity, could be used as the device for recovering serum. Such devices are described in DE-U-29 516 471, EP-A-0 266 683, EP-A-1 089 778, EP-A-1 309 363, U.S. Pat. No. 4,639,243 or WO 2011/157822, for example.

These devices, like the present device for recovering serum from whole blood, include a blood bag for receiving a sufficient quantity of whole blood; a filter module connected to the blood bag, in which a separation of the blood into blood plasma and erythrocyte concentrate takes place in the event of plasma separation, wherein in this application, a separate discharge of these components into corresponding receiving bags is accomplished.

As in the previously mentioned plasma separation using the effect of gravity, in the present system for wound treatment, serum can be recovered and delivery of the serum into the wound region can also be accomplished by the effect of gravity, meaning without additional pumping or by application of pressure or the like. To this end, in application blood bag and filter module could be arranged via an appropriate holding device at a defined vertical distance from one another and over the wound, so that the outflow from the blood bag into the filter module, and further from the filter module and through the first capillary membrane system into the wound region, can be carried out under the influence of gravity.

For the present device for recovering serum, in application the blood bag is filled with a predetermined quantity of whole blood. The blood located in the blood bag is then subjected to coagulation or blood clotting. Coagulation is a complex procedure that runs like a chain reaction with the participation of different clotting factors (such as thrombocytes, fibrinogen, calcium and vitamin K). Coagulation of the blood is triggered by the drawing of blood and the absence of anticoagulant agents such as citrate or heparin in the blood bag.

As a consequence of blood clotting, the blood separates into a solid fraction (coagulum), which contains the cellular components such as red blood cells, blood platelets and white blood cells, and a fluid phase, which contains all dissolved substances naturally occurring in the blood fluid except for the clotting factors consumed in clotting. The solid fraction is present here as a gelatinous mass.

The blood bag of the present device for recovering serum comprises a barrier in the region of its outlet that is appropriate for retaining at least the majority of the solid fraction, meaning the coagulum present in the form of a gelatinous mass. For this, the barrier can be a narrowing in the region of the outlet that permits passage of the fluid fraction. The barrier can also be a clamp that has a sufficiently large gap in the region of the outlet for the passage of the fluid out of the blood bag.

The outlet of the blood bag is fluidically connected to the filter module of the device for recovering blood serum, for example via an appropriate tube section, wherein the connection between the blood bag and the filter module is preferably designed to be releasable, for example via appropriate male/female connectors in the form of Luer lock connectors, for instance. Alternatively, the connection between blood bag and filter module, that is, ultimately between blood bag and tube section, between tube section and filter module, or between partial sections of the tube section, may also be designed as a sterile welded joint as they can be produced via a sterile connector (for example TSCD® II Sterile Tubing Welder, Terumo Co.). For its part, the filter module or the permeate outlet of the filter module is fluidically connected to the first capillary membrane system via the permeate line, which includes at least one supply line of the first capillary membrane. The connection between permeate outlet of the filter module and first capillary membrane is preferably also detachable, for example via appropriate male/female connectors, which may preferably be Luer lock connectors or may be designed as a sterile welded joint as can be created via the aforementioned sterile connectors. A break-open valve can be arranged in the permeate line so that a targeted addition of serum can be performed at a defined point in time.

The semipermeable membrane arranged in the filter module or in the interior of the housing of the filter module can be designed in the form of a flat membrane or a hollow-fiber membrane. The semi-permeable membrane is preferably a bundle of hollow-fiber membranes. In this event, the retentate space is formed by the lumina of the hollow-fiber membrane, and the permeate space is formed by the outer space that surrounds the hollow-fiber membranes and is delimited by the interior wall of the housing. In an especially preferred embodiment, the bundle of hollow-fiber membranes arranged in the filter module has a U-shaped design. In this event, the housing of the filter module has a cover and a floor, and the inlet device for introducing the fluid discharged from the blood bag into the retentate space as well as the retentate outlet for discharging the retentate from the retentate space are arranged on the cover side. The permeate outlet for discharging the permeate, meaning the serum, from the permeate space is arranged on the floor side in this filter module.

In order to be able to generate a high enough permeate flow through the semipermeable membrane of the filter module, in particular when recovering serum using the force of gravity, the semipermeable membrane of the filter module preferably has a trans-membrane flow ranging from 10,000 to 40,000 l/($m^2 \cdot h \cdot bar$). In a further preferred embodiment, the semipermeable membrane of the filter module has a nominal pore of 0.2 µm. The nominal pore for this is defined via the retention capacity of the membrane with respect to specific microorganisms. Membranes having a nominal pore of 0.2 µm are generally designated as bacteria-proof because they retain bacteria of the genus *Brevundimonas diminuta*. Naturally, they also retain bacteria of, for example, the genus *Serratia marcescens*, for which a nominal pore of 0.45 µm would be sufficient. The testing or determination of the nominal pore sizes are described, for example, in the HIMA regulations No. 3, Vol. 4, 1982 (Health Industry Manufacturers Association).

As stated, the permeate outlet of the filter module of the device for recovering serum is in fluidic connection with the first capillary membrane system via the permeate line, which includes at least one supply line of the first capillary membrane. In a preferred embodiment, at least one receptacle for receiving either the permeate or the serum exiting the filter module can be arranged in the permeate line, the receptacle having an inlet and an outlet. The inlet of the receptacle is thus connected to the permeate outlet of the filter module via a partial section of the permeate line facing toward the filter module, and the outlet of the receptacle is connected to the first capillary membrane via a discharge line as part of the permeate line.

In an additional advantageous embodiment, the receptacle comprises a plurality of partial receptacles that are arranged in a parallel connection to one another. The outlets of the partial receptacles are each connected to a discharge line that is ultimately connected via a connection element to the supply line of the first capillary membrane system To do this, the discharge lines preferably each have a control element by which the individual partial receptacles can be connected or disconnected, or by means of which the flow through the line can be set to defined values. Such an embodiment is particularly advantageous if, for example, the serum created in the filter module is to be divided into aliquots among a plurality of partial receptacles, in order to subsequently supply the aliquots of the serum sequentially at specified time periods during wound treatment.

In a preferred embodiment, in addition to the first capillary membrane the present system for wound treatment using a serum comprises at least one additional capillary membrane having a planar configuration, by means of which the wound can be supplied with additional fluids or active substances or gases, or by means of which fluids may be removed from the wound region. In a particularly preferred embodiment, the present system for wound treatment comprises a second capillary membrane system having a planar configuration that is connected to at least one supply line, so that fluids, media, gases and/or other materials can be conducted through the supply line and the second capillary membrane; as well as a discharge receptacle which is detachably connected via a conduction path—which includes at least one of the supply lines of the second capillary membrane system—to the second capillary membrane system, and via which the second capillary membrane system can be supplied with irrigation fluid. Additionally, the system for treating wounds can comprise a drainage system that can be coupled to a negative pressure unit and by which fluids can be carried away from the wound to be treated.

In application, the first and, if needed, the second capillary membrane systems can be inserted into the wound and, as already stated, be covered, for example by a semi-occlusive, transparent film, in order to protect the wound from drying out or from infection. The supply lines of the capillary membrane systems are then routed out of the wound region under the film and are connected to the filter module of the device for recovering serum, or to the respectively associated dispenser containers etc. The optionally present drainage system can be connected to a negative pressure unit via, for example, an appropriate tube that is stable with respect to negative pressure and is likewise routed out of the wound region.

To do this, the first capillary membrane system, or any additional capillary membrane systems having a planar configuration that may be present (described below as the at least one capillary membrane system), can in each case be made up of a single capillary membrane that is arranged in a meandering form. In this embodiment, at least one of the ends of the meandering capillary membrane is open and connected to a supply line. However, the at least one capillary membrane system may also include a plurality of capillary membranes arranged in a meandering configuration that, together with their ends, open into a common supply line. Preferably, the at least one capillary membrane system includes a plurality of capillary membranes arranged parallel to one another.

The capillary membranes of each capillary membrane system, said capillary membranes being arranged parallel to one another, are embedded in a fluid-tight manner at least at one of their ends in the wall of a supply line on their outer periphery, in such a manner that there is a fluidic connection between the lumen of the supply line and the lumen of the capillary membrane, and such that fluids, media, gases and/or other materials can be conducted through the supply line and the at least one capillary membrane system. The embedding can be done using a curable silicone material, a polyurethane or an epoxy resin, for example. Curable silicone materials are preferably used because of their better flexibility. In the event that the capillary membranes are only embedded with one of their ends in the supply line, the other, opposite end of the capillary membranes is closed, for example by welding or gluing. The capillary membranes can also be embedded open at their two ends and with these two ends on one side of the arrangement in a single supply line, wherein the capillary membranes are then U-shaped at their open ends and thus are closed there. In these cases, the capillary membranes operate in dead-end mode.

In particular in the event of wider wound care systems, embodiments of the capillary membrane systems having capillary membranes arranged parallel to one another are advantageous, in which the capillary membranes are open at their two ends and are embedded in each case in a supply line, wherein the supply lines are then preferably located on opposite sides of the respective capillary system having a planar configuration. In this event as well, the embedding is designed in such a manner that the capillary membranes are embedded fluid-tight on their outer periphery, and such that there is a fluidic connection between the lumen of the respective supply line and the lumen of the capillary membranes. Such an embodiment having two supply lines allows for supply and/or drainage via the at least one capillary membrane system in a cross-flow mode. Also with a view toward good homogeneity of supply or drainage across the surface of the wound, the implementation of at least one capillary membrane system having two supply lines may be appropriate, especially in wider mats or wound care systems. An embodiment having two supply lines, however, also allows a simultaneous or even alternating supply to a wound with different media via the same capillary membrane system.

The diameter of the supply lines is primarily directed to the outer diameter of the capillary membranes embedded in it. Therefore, the at least one supply line preferably has an inner diameter ranging from 0.1 to 10 mm. It is likewise preferred if the wall thickness ranges from 0.1 to 5 mm. In the event in which a supply line having a non-circular cross-section is used, the equivalent diameter $d=4 A/U$ of the inner cross-section is assigned as the inner diameter, with A as the area of the inner cross-section and U as its circumference. For example, the supply line can also have an oval or approximately square or rectangular inner cross-section. Silicone tubes, for example, have shown themselves to be appropriate for supply lines through whose wall the capillary membranes pass and in which they are adhesively fixed. The supply lines are preferably made from a flexible silicone tube. The embedding or gluing into the wall of the supply line can be accomplished using a common glue such as a curable silicone material, polyurethane resin, or an epoxy resin.

In an advantageous embodiment, the at least one capillary membrane system can be designed in the shape of a mat made from capillary membranes arranged parallel to one another, wherein the capillary membranes are connected to one another in the mat via connecting elements running spaced from one another and parallel to one another, and are maintained at a distance from one another via the connecting elements. The connecting elements can run transversely to the parallel membranes arranged parallel to one another, or also at a different angle. The connecting elements then touch the capillary membranes at their outer periphery or wrap around them. The connecting elements have no closed flow channels along their length, and consequently fluid therefore cannot flow through them. The connecting elements can be adhesive strips or, for example, can also be strand-like elements made from a silicone material. In a preferred embodiment, the capillary membranes are connected into a mat using yarn-like connecting elements. The connecting elements are especially preferably textile multifilament yarns. Multifilament polyester yarns, polypropylene yarns or polytetrafluorethylene yarns have proven particularly advantageous as textile multifilament yarns. The most appropriate are hydrophilic yarns, preferably made from polyester.

In a preferred embodiment, the capillary membrane mat can be a knitted mat. In such knitted mats, the capillary membranes and the connecting strands are knitted together and the capillary membranes run transversal to the extension direction of the capillary membrane mat. The length of the capillary membranes is determined by the mat width. In a further preferred embodiment, the capillary membrane can be a woven mat. In such woven mats, the capillary membranes and the connecting strands are woven together. The capillary membranes in this run in the extension direction or running direction of the capillary membrane mat, and the textile strands run transversal thereto. Knitted and woven capillary membrane mats, as well as the options for their manufacture, are described in DE 38 39 567, DE 43 08 850 and EP 0 442 147, for example. Especially when using knitting technology, mats in which the capillary membranes are formed in a U shape at their free ends and are closed there can be manufactured in a simple manner. Mats of this type can be manufactured via meandering placement of a capillary membrane in strands parallel to one another that are connected to one another by the knitting strands. In this process, the U-shaped ends formed on at least one side of the knitted mat are trimmed off after finishing the knitted mat, and the resulting open ends of the capillary membranes are then embedded in a supply line. In the event that the U-shaped ends are trimmed off on both sides of the knitted mat, the resulting opposing open ends are then each embedded in supply lines.

In a preferred embodiment, the capillary membranes are located inside the mat in such a density that the spacing of the mats from one another inside the mat amounts to 1 to 10 times the outer diameter of the capillary membranes, wherein the distance is measured from the longitudinal axes of the capillary membranes. Mats are thereby preferred in which the spacing of the capillary membranes from one another inside the mat amounts to 1.05 to 6 times the outer diameter of the capillary membranes. Distances of the capillary membranes from one another inside the mat that range from 1.05 to 3 times the outer diameter of the capillary membranes are especially preferred. In an additional especially preferred embodiment, distances of the capillary membranes from one another inside the mat are more than 1.5 times the outer diameter of the capillary membranes. It was found that a certain separation of the capillary membranes from one another can be achieved in this way.

At the same time, with regards to a good homogeneous supply to the wound to be treated, it can be important that the capillary membranes in the capillary membrane systems are connected together into a mat via a plurality of connecting elements that are spaced apart from and run parallel to one another, and are kept at a distance from one another via the connecting elements, and that the connecting elements are located at a defined distance from one another that preferably ranges from 1 to 50 mm, wherein a spacing in the range from 3 to 20 mm is especially preferred and one ranging from 4 to 6 mm is most suitable. Namely, it has been shown that the contact points between the capillary membranes and the connecting elements to a significant extent promote distribution of the fluid over the surface of the arrangement of the capillary membranes when, for example, the wound to be treated is supplied with a treatment solution or a nutrient solution, for example. It was thus observed that the application of such capillary membrane systems onto wounds to be treated results in an improvement in the exiting of fluid from the capillary membranes at the contact sites.

The capillary membranes of the at least one capillary membrane system preferably have an outer diameter ranging from 200 to 1500 µm. Likewise, capillary membranes having a wall thickness ranging from 20 to 400 µm are advantageous, wherein there outer diameter can preferably be located in the aforementioned ranges.

In the present wound care system, the at least one capillary membrane system can be designed for the supply or discharge of fluid media. In order to ensure a uniform supply of the wound to be treated, in a preferred embodiment the capillary membranes in this event have a high permeability to fluids. The trans-membrane flow for water of the capillary membranes is preferably within the range from 0.01 to 50 ml/(min·cm$^2$·bar). As will be described later, it is possible, however, for the wound care system to include capillary membrane systems that serve to supply oxygen to the wound or to regulate pH value, for example.

The capillary membranes of the at least one capillary membrane system are preferably bacteria-tight. In this manner, it can be guaranteed that no bacteria arrive in the wound via a supply of irrigation fluids and/or other treatment solutions, for example. As previously described, within the context of the present invention "bacteria-tight" is thereby understood to mean that the capillary membranes have a nominal pore of 0.2 µm. Preferably, the capillary membranes of the first and/or the second capillary membrane systems also have a nominal pore of 0.2 µm.

As materials for the capillary membranes of the capillary membrane systems, but also for the semipermeable membrane of the filter module, in principle all organic polymers known in the prior art can be considered that are suitable for the formation of capillary membranes in particular, wherein these polymers must have good biocompatibility. Beyond that, it is also necessary that the membrane polymer permits sterilization of the wound care system and of the filter module, for example by steam sterilization, sterilization using γ-radiation or sterilization using ethylene oxide. The organic polymers can be natural polymers or polymers that are created in a synthetic manner. Natural polymers are in particular those based on cellulose polymers, which also includes polymers that have undergone what are known as polymer-analogous reactions. Examples of polymers based on cellulose are those made from regenerated cellulose, cellulose acetate or modified cellulose such as cellulose ester, cellulose ether, cellulose modified using benzyl groups (benzylcellulose) or cellulose modified using diethylaminoethyl, or mixtures of these cellulose polymers. Furthermore, polymers based on chitin or chitosan can also be used.

As polymers manufactured in a synthetic manner, meaning synthetic polymers, those that can be used are the ones composed of polyolefins, polyamides, polyacrylonitriles, polycarbonates, polyesters or sulfone polymers, as well as modifications, blends or copolymers obtained from these polymers. Advantageously used are those that are based on sulfone polymers, such as polysulfone or polyethersulfone in particular.

Additional polymers such as polyethylene oxide, polyhydroxylether, polytheleneglycol, polyvinyl alcohol or polycaprolactone can be mixed into the synthetic polymers as additives. In addition, the capillary membranes can also have a coating with an additive. Such capillary membranes preferably contain a hydrophilizing agent such as polyvinylpyrrolidone, or also hydrophilic modifications of these polymers.

The capillary membranes of the capillary membrane systems can be modified via linking of functional groups, for example, with an eye to specific applications, or be coated using heparin, for example, or an antibiotic or a plurality of antibiotics.

The shape of the capillary membrane having a planar configuration can vary in its planar extension. In the event of capillary membrane systems made from capillary membranes parallel to one another, the capillary membrane systems in the simplest version have a square or a rectangular shape. It is also possible, for example in systems in which the capillary membranes are only embedded at one of their ends in a supply line, that an arc-shaped contour can be formed, for example via correspondingly adapted welding of the free, closed ends of the capillary membranes parallel to one another. It is likewise possible that the arrangement of capillary membranes parallel to one another also has a trapezoidal contour, for example.

As already indicated, the present wound care system can also have additional components such as at least one additional arrangement of capillary membranes. The capillary membranes of the additional arrangement can be membranes for oxygenation, for example, meaning membranes via which oxygen can be supplied to the wound. Membranes of this type are disclosed in EP-A-1 144 096, EP-A-0 299 381 or DE-A-28 33 493, for example. Also possible is a combination with additional systems having a planar configuration or an arrangement of semipermeable capillary membranes or fluid-impermeable capillaries, via which tempering or pH value regulation can be performed. The respective capillary membrane systems and any additional systems of semipermeable capillary membranes or fluid-impermeable capillaries having a planar configuration can then be stacked on one another. However, it is also possible that, for example, the capillary membranes of different capillary membrane systems can be connected together to form a mat, wherein the different capillary membranes are arranged having their ends embedded in different supply lines, which are preferably arranged on opposites sides of the mat. Such mats can be obtained by knitting together meandering capillary membranes that are arranged offset from one another, in which the U-shaped connections of the capillary membranes are located at different positions across the width of the mat. By cutting the respective outer U-shaped connections, the capillary membranes are each opened on only one side of the mat and can be embedded there in a supply line.

In the preferred embodiment in which, in addition to the first capillary membrane system and optionally a second capillary membrane system, the system for wound treatment or the wound care system comprises a drainage system by means of which a discharge of irrigation fluid or of exudate from the wound is possible, for example, the drainage system can include an absorbent sponge that possesses a suction line for the irrigation fluid and/or exudate. The drainage system can also be designed as an additional capillary membrane system. However, the drainage system is preferably at least one drainage catheter, for example in the form of a tube piece made of a silicone material, for example, or in the form of a small pipe. Such a drainage catheter can have perforations in its wall through which fluids can be suctioned from the wound after connection of the drainage catheter to a negative pressure unit. The at least one drainage catheter preferably has an inner diameter ranging from 0.1 to 15 mm and a wall thickness ranging from 0.1 to 3 mm. The drainage catheter can also have a non-circular cross-section. In this event, the equivalent diameter $d_D = 4 A_D/U_D$ of the inner cross-section is used as the inner diameter, with $A_D$ being the area of the inner cross-section of the drainage catheter and $U_D$ being its circumference.

In one embodiment, the wound care system may additionally include a pocket-shaped wound dressing, wherein the pocket-shaped wound dressing is closed at its outer edge and has a top side, a bottom side and a pocket interior, wherein the bottom side and the top side are each formed of a sheet-like material and the bottom side is permeable to fluid, and wherein the first and any additional capillary membrane systems are arranged in the pocket interior. Here the connection of the supply lines with the filter module and any receptacles etc. is situated outside the pocket-shaped wound dressing.

The pocket-shaped wound dressing, including the capillary membrane system contained therein, can be inserted into the wound to be treated in such a way that the bottom side is in contact with the wound. Via the capillary membrane system, the wound can be provided with the desired fluids, which are distributed in the pocket after exiting from the capillary membranes and are dispensed to the wound via the semipermeable bottom side of the pocket.

The pocket-shaped wound dressing can preferably be designed so that the connection of the capillary membranes of the capillary membrane systems to the corresponding supply line is located in the pocket interior, and the corresponding supply lines lead out of the pocket-shaped wound dressing via fluid-tight adapted passage openings on its outer cross-section. Similarly, the connection of the capillary membranes to the corresponding supply line can be arranged outside the pocket-shaped wound dressing, on the top side, and the arrangement of the capillary membranes for connecting to the at least one supply line can lead out of the pocket-shaped wound dressing via a fluid-tight adapted passage opening.

In the event that the wound care system comprises a pocket-shaped wound dressing, the capillary membrane systems extend two-dimensionally within the interior of the pocket. The dimensions of the capillary membrane systems respectively result from their outer measurements in the planar extension. With respect to its planar extension, the at least one capillary membrane system preferably fills the interior of the pocket of the pocket-shaped wound dressing in its planar extension, at least to 20% and particularly preferably at least to 50%. It is a particular advantage if the at least one capillary membrane system, with respect to its planar extension, fills the pocket interior of the pocket-shaped wound dressing to at least 70%, wherein a degree of filling in the range of 90% can also be realized. It is thereby advantageous if the at least one capillary membrane is arranged centrally in the pocket-shaped wound dressing.

The pocket-shaped wound dressing can have arbitrary contours. However, the contour is preferably round, oval, square or rectangular. The bottom and top side of the pocket-shaped wound dressing are connected with one another at the outer margin or on the outer edges of the wound dressing, for example by welding or adhesion. Among other things, silicone strips that are cured are appropriate for adhesion. In the event of rectangular or square pocket-shaped wound dressings, the capillary membranes systems having a planar configuration arranged therein also preferably have a rectangular or a square contour. In the event of round or oval pocket-shaped wound dressings, the capillary membrane systems contained therein are advantageously also designed as a square or as a rectangle, wherein the aforementioned dimensions are likewise valid as measurements. However, they can also be adapted to the contour of the pocket-shaped wound dressings, for example by correspondingly adapted welding of the non-embedded ends of the capillary membranes in capillary membrane systems having only one supply line each, so that an arc-shaped contour results at these edges of the capillary membrane systems.

The bottom side of the pocket-shaped wound dressings is transmissive with respect to fluids, meaning permeable. The bottom side can thereby be made of a fleece-like, flat material, a mesh- or net-like material, a perforated film or a semipermeable, microporous planar membrane, for example. In an advantageous embodiment, the bottom side comprises a fleece-like, flat material or a semipermeable, microporous planar membrane. The bottom side preferably has a permeability to water of at least 0.01 ml/(min·cm²·bar), and particularly preferably of at least 10 ml/(min·cm²·bar). A bottom side with a permeability to water of at least 500 ml/(min·cm²·bar) has proven to be best.

For the intended applications of the wound care system, in which the wound is not only supplied with fluid via the wound care system but a removal should take place, meaning a discharge of fluids from the wound via the drainage system, it is advantageous if openings are present on the bottom side, wherein the openings preferably have a diameter of at least 100 µm. Opening diameters of at most 10 mm are thereby preferred, particularly preferably of no more than 5 mm. In the event that the bottom side is made of a semipermeable, microporous membrane, in one advantageous embodiment this has additional openings, for example in the form of perforations. In the event that the openings have a non-circular contour, the equivalent diameter D=4 A/U of the opening is used as the diameter, with A as the area of the respective opening and U as its circumference. The openings can be regularly or irregularly distributed across the surface of the bottom side, wherein a regular, homogeneous distribution is preferred. The distance between the openings can thereby range from 1 to 20 mm, as measured from the outer edge of the openings.

The bottom and top sides of the pocket-shaped wound dressing can be made of the same or different materials. However, while the bottom side is always permeable to fluids, the top side is preferably formed from a fluid-impermeable, preferably film-like material that is connected fluid-tight to the bottom side on its or their side edges. The top side can also be made from a semipermeable, microporous planar membrane. In this event, however, the top side has a lower permeability with respect to fluids than the bottom side, in order to ensure in application a distribution of supplied fluids to the bottom side of the pocket-shaped wound dressing, and thus to the wound. In the event that the bottom side and the top side are made from the same or identical semipermeable, microporous planar membrane, the bottom side has perforations.

In principle, the same organic polymers as were previously mentioned as polymers for the capillary membranes and that can be processed into planar films or planar membranes are conceivable for the bottom or top side of the pocket-shaped wound dressing. The bottom and/or top side of the pocket-shaped wound dressing are preferably constructed out of polyolefins, polyamides, polyacrylonitrile, polycarbonates, polyesters or sulfone polymers as well as modifications, blends or copolymers derived from these polymers. Particularly preferably, the bottom and top sides include sulfone polymers as a material, wherein polysulfone or polyethersulfone are most suitable.

In the preferred instance—that the wound care system comprises a pocket-shaped wound dressing—the drainage system provided according to one embodiment, preferably in the form of at least one drainage catheter, leads out of the pocket-shaped wound dressing via a corresponding fluid-tight, adapted passage opening and is connectable to a negative pressure unit outside the pocket-shaped wound dressing in order to create a negative pressure in the interior of the pocket during application.

The at least one drainage catheter can be a tube section made of a silicone material, for example, or a small pipe that is arranged in the interior of the pocket of the wound dressing and leads out of the wound dressing via the passage opening. At the segment of the at least one drainage catheter that is located in the interior of the pocket-shaped wound dressing, said drainage catheter preferably has perforations in its wall through which fluids, for example also exudate or supplied serum, can be suctioned out of the wound or out of the interior of the pocket-shaped wound dressing and from the wound after connection of the at least one drainage catheter to a negative pressure unit.

In a preferred embodiment, the first and the second capillary membrane systems of the wound care system are identical and form a single supply capillary membrane which is connected to at least one supply line, and the device for recovering serum and the dispenser container connected to the second capillary membrane system are connected to the supply capillary membrane system via the at least one supply line of the supply capillary membrane system. The supply capillary membrane system can thereby have two supply lines that are located at the opposite ends of their capillary membranes. In this event, for example, the device for recovering serum and the dispenser container, which preferably includes an irrigation fluid, can be connected to different supply lines that are separated from one another. It is also possible, however, that the device for recovering serum and the dispenser container are connected to only one supply line of the supply capillary membrane system, for example via line sections that are connected to one another via a T-joint or a Y-connector. Embodiments of the supply capillary membrane system in which the supply capillary membrane system is connected to only one supply line are also possible here.

It is preferable for the application if, for example, the irrigation fluid from the dispenser container and the serum from the filter module can be supplied in an alternating manner.

The line path between the filter module and the capillary membrane system connected to the filter module preferably has a first valve assigned to the filter module. Likewise, the line path between the indicated dispenser container and the capillary membrane system connected to the dispenser container has a second valve associated with the dispenser container, wherein the first and the second valves can be adjusted independently of one another. Depending upon the design of the wound supply system, the valves can be placed at the filter module or the dispenser container themselves; in the line sections between filter module or dispenser container and a T-joint or Y-connector that connects the line sections of filter module and dispenser container; or in the respective supply line.

In a preferred embodiment, the filter module and dispenser container are detachably connected to the corresponding supply line via male/female connectors. The male/female connectors are particularly preferably Luer lock connectors. Here, too, the connection can be designed as a sterile welded connection as it can be produced using the aforementioned sterile connectors.

Typical fluids that are appropriate for cleaning wounds can be used as irrigation fluids that can be supplied, as mentioned, via the second capillary system. The dispenser container connected to the second capillary membrane system preferably contains a saline solution. For example, additional treatment solutions, such as solutions having growth factors, antibiotics or solutions containing other medicines, solutions for pH-value regulation, can be supplied to the wound via additional capillary membrane systems.

In order to characterize the properties of the capillary membranes or planar membranes used in the wound care system, the following measurement methods are used as a basis:

Trans-membrane flow (water permeability) for capillary membranes:

A test cell having a defined number and length of capillary membranes is made from the capillary membranes to be tested. For this, the capillary membranes are embedded at their ends on both sides in a polyurethane resin. After the resin cures, the embeddings are cut to a length of approximately 30 mm, wherein the lumina of the capillary membranes are opened by the cutting. The capillary lumina in the embeddings must be checked for continuity. The free length of the capillary membranes between the embeddings is usually 120+/−10 mm. The number of capillary membranes is to be dimensioned so that, taking into account the free length and the internal diameter of the capillary membranes, a filtration area of approximately 30 cm² is provided in the test cell.

The test cell is integrated into a testing apparatus and is perfused with ultra-filtered and demineralized water tempered to 25° C. at a specified test pressure (approximately 0.4 bar). The amount of filtered water obtained during a measurement time of 2 minutes, meaning the permeate created during the measurement, is gravimetrically or volumetrically recorded. Before the start of the measurement, the equipment must be purged of air. In order to determine TMF, the input and the output pressure of the test cell are measured in the testing apparatus. The measurement is conducted at a temperature of 25° C.

The trans-membrane flow TMF is determined according to the formula (I)

$$TMF = \frac{V_W}{\Delta t \cdot A_M \cdot \Delta p} \left[ \frac{ml}{cm^2 \cdot min \cdot bar} \right] \qquad (I)$$

In which:
$V_W$=water volume [ml] flowed through the membrane specimen during the measurement time
$\Delta t$=measurement time [min]
$A_M$=area of the membrane specimen (generally 30 cm²) through which water flowed
$\Delta p$=set pressure during the measurement [bar]

Permeability to Water of the Bottom Side of the Pocket-Shaped Wound Dressing:

Disc-shaped specimens are stamped out of the planar material to be tested from the bottom side of the pocket-shaped wound dressing and are clamped into a suitable specimen holder that is fluid tight at the perimeter, so that a free measurement area of 17.35 cm² results. The specimen holder is located in a housing through which water can flow when pressure is applied. Demineralized water at a temperature of 25° C. and at a defined pressure between 0.1 and 0.2 bar then flows through the clamped specimen. The water volume that flowed through the specimen during a measurement time of 60 seconds is gravimetrically or volumetrically determined.

The permeability to water $TMF_W$ is determined according to the formula (II)

$$TMF_W = \frac{V_W}{\Delta t \cdot A_M \cdot \Delta p} \left[ \frac{ml}{cm^2 \cdot min \cdot bar} \right] \qquad (II)$$

In which:
$V_W$=water volume [ml] flowed through the specimen during the measurement time
$\Delta t$=measurement time [min]
$A_M$=area of the specimen (17.35 cm²) through which water flowed
$\Delta p$=set pressure during the measurement [bar]

The invention is explained in detail in reference to Figures below, wherein the scope of the invention is not limited by Figures.

Shown are.

Figure 1:
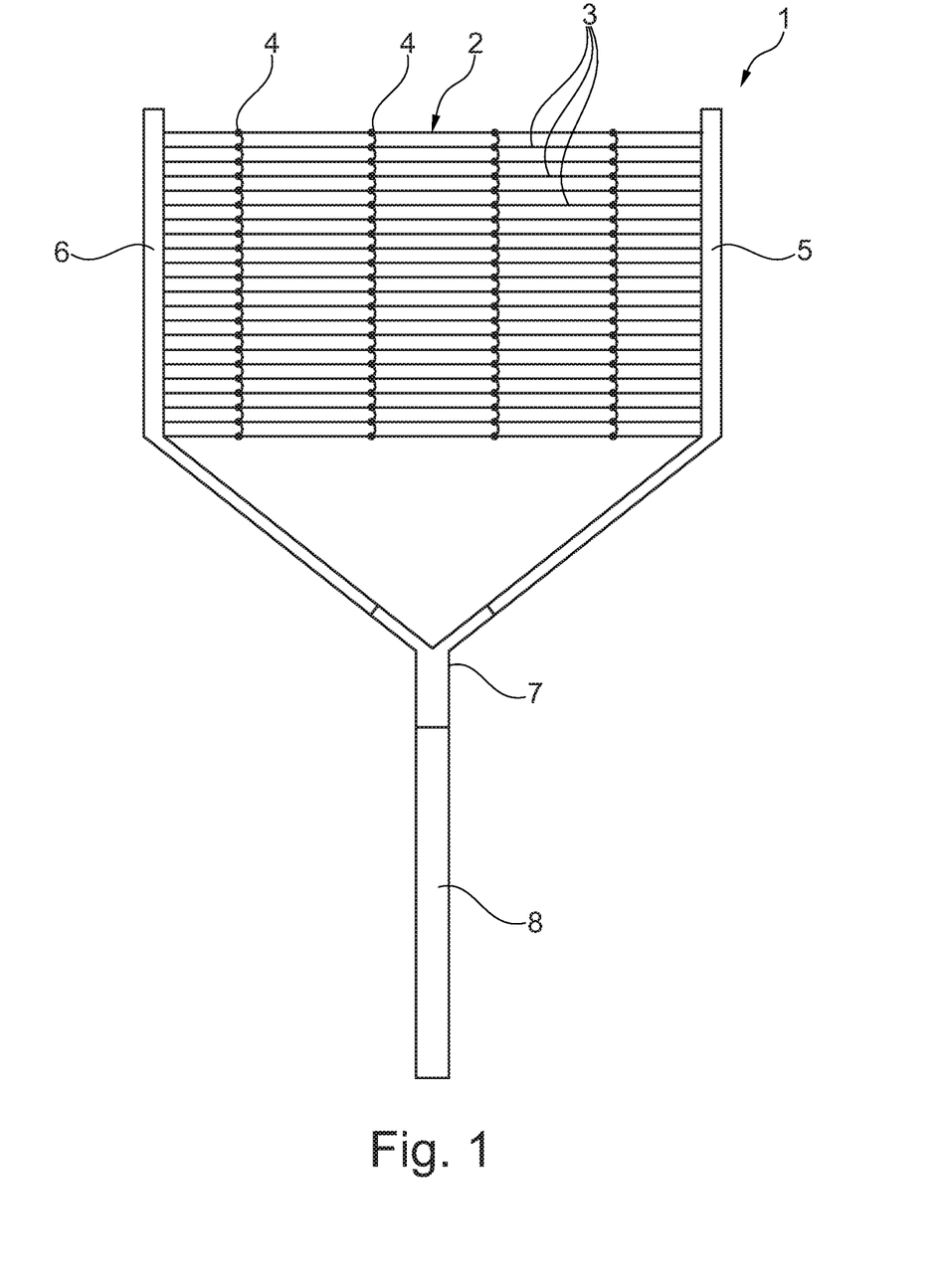
FIG. 1: a wound care system having a single-layer mat made from capillary membranes and supply lines at both ends of the mat.

FIG. 1 shows in plan view, schematically and not to scale, a wound care system 1 that can be used in a system for wound treatment according to the invention, having a capillary membrane system 2 made from capillary membranes 3. The capillary membranes 3 are connected via connecting elements 4 that run parallel to one another to form a mat, in such a manner that they are arranged parallel to one another and are maintained at a distance from one another. The capillary membranes 3 in the present example have their opposing ends embedded in supply lines 5, 6 in such a manner that there is a fluidic connection between the lumina of the supply lines 5, 6 and the lumina of capillary membranes 3. The supply lines 5, 6 are merged via a Y-piece 7 into a common supply line 8. The result of this design is, for example, that serum which is supplied via line 8 is distributed between supply lines 5, 6 and supplied to capillary membranes 3 in a dead-end mode. The serum flows out of the capillary membranes 3 across their porous, semipermeable walls and is uniformly supplied to the wound over the surface of the arrangement 2 made from capillary membranes 3.

Figure 2:
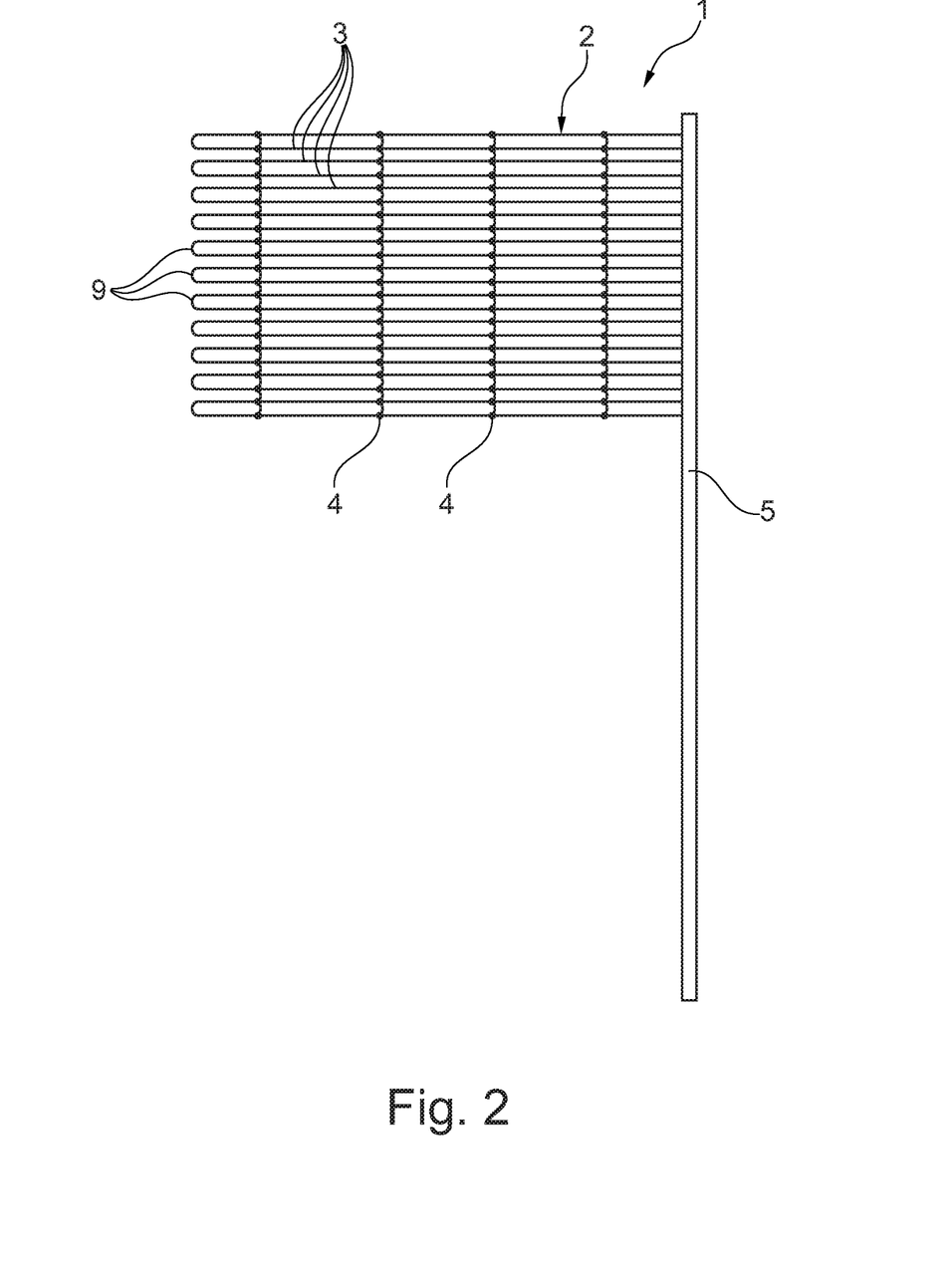
FIG. 2: the wound care system having a supply line at one of the mat ends, as well as U-shaped capillary membrane ends at the opposite end of the mat.

FIG. 2 also shows in plan view, schematically and not to scale, a wound care system 1 in which the capillary membranes 3 are only connected to one supply line 5. The capillary membranes are open at both of their ends and are embedded with both of their ends in one supply line 5. The free ends 10 of the capillary membranes 3 are formed into a U shape at the end of the mat that is opposite the supply line 5, and are thereby closed. In this manner, the incident flow takes place in dead-end mode in the capillary membranes 3 of the wound care system 1 shown in FIG. 3.

Figure 3:
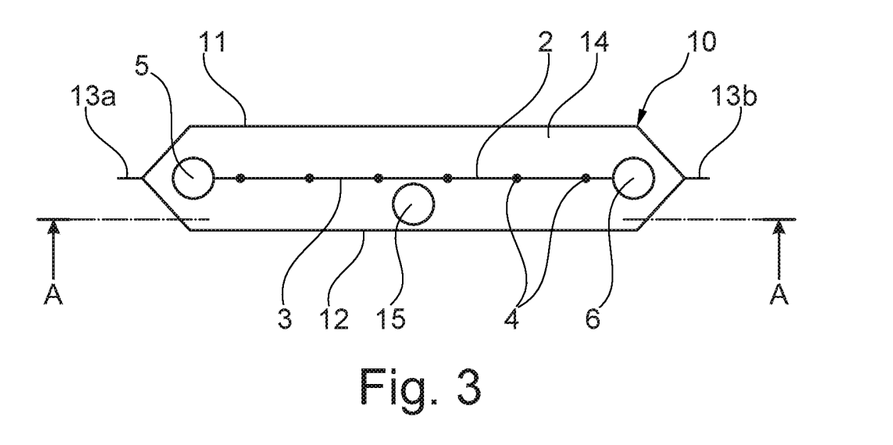
FIG. 3: cross-section (schematic) through a pocket-shaped wound dressing system that can be used in a system for wound treatment.

FIG. 3 schematically shows a cross-section through a pocket-shaped wound dressing 10, which has a top side 11 and a bottom side 12 that are welded together at their edge 13a, 13b, whereby a closed pocket interior 14 is formed. Arranged in the interior of pocket 14 is a first planar capillary membrane system 2, which includes capillary membranes 3 that are connected together and maintained at a distance from one another via connection elements 4 which run parallel to one another, preferably in the form of multifilament yarns. Where necessary, in one embodiment a required second capillary membrane system according to the present invention can be arranged above or below the illustrated capillary membrane system 2, wherein the supply lines of the first capillary membrane system and of the second capillary membrane system can then be routed out of the pocket-shaped wound dressing 10 on the same side or on different sides of this.

In the present case, the capillary membranes 3 open at their opposing ends into supply lines 5, 6 so that fluids, media, gases and/or other substances can be conveyed via the supply lines 5, 6 and the capillary membrane system 2. Supply lines 5, 6 are routed out via the top side 11 of pocket-shaped wound dressing 10 (not shown here).

Arranged below the planar capillary membrane system 2 is a drainage tube 15 through which exudate that has collected in the wound, for example, may be removed.

Figure 4:
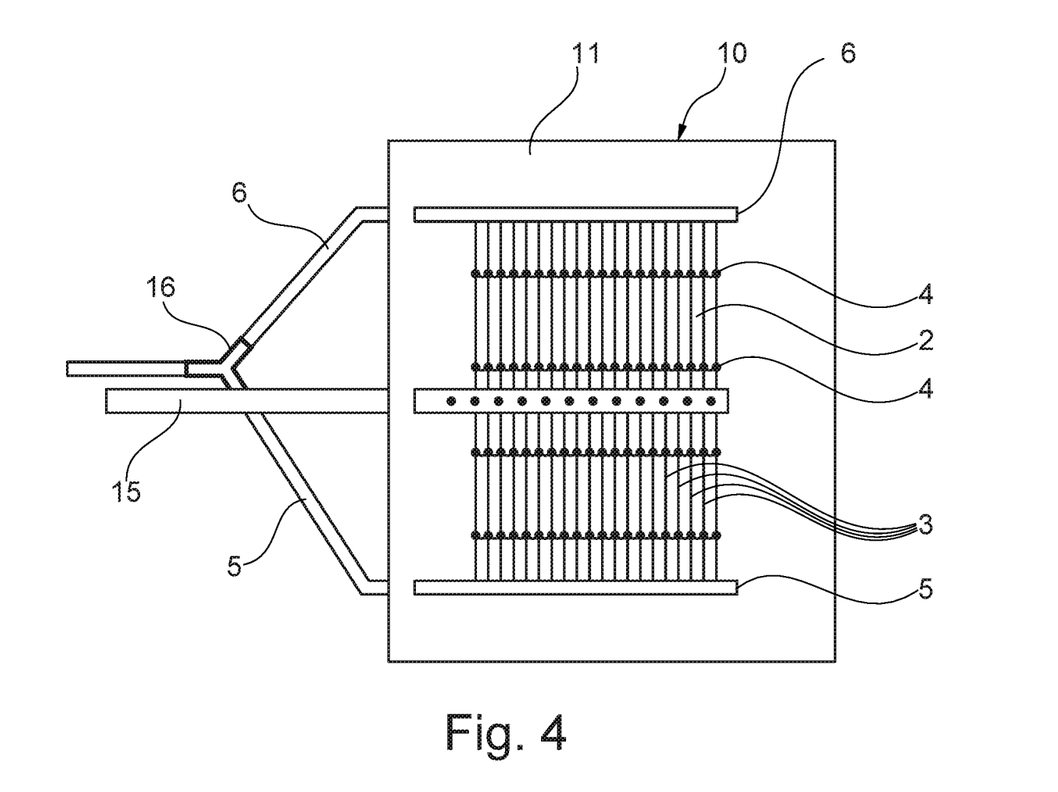
FIG. 4: section A-A of the pocket-shaped wound dressing system shown in cross-section in FIG. 3.

FIG. 4 shows the wound dressing system illustrated in FIG. 3 in a cross-section along the line A-A. It is essentially a plan view from a position above bottom side 12 of pocket-shaped wound dressing 10 in the direction of the top side 11 of said pocket-shaped wound dressing 10. Arranged below the top side 11, meaning as shown in FIG. 3, between bottom side 12 and top side 11 is the capillary membrane system 2, which is constructed from capillary membranes 3 that are parallel to one another and are connected together and held at a distance from one another by connecting elements 4. Capillary membranes 3 are embedded with their opposite ends in the supply lines 5, 6 so that fluids, media, gases and/or other substances can be passed through the supply lines 5, 6 and the capillary membranes system 2. Supply lines 5, 6 are passed through the top side 11 of the pocket-shaped wound dressing 10, through correspondingly adapted openings in the top side 11 of the pocket-shaped wound dressing 10, and, in the present example, are merged via a Y-connector 16 outside of the pocket-shaped wound dressing 10. In the present case, the capillary membrane system 2 is thus operating in dead-end mode, meaning that a medium supplied via the supply lines 5, 6 is introduced into the capillary membrane system 2 and fully enters into the interior of the pocket via the walls of the capillary membranes 3.

Also illustrated in FIG. 2 is drainage tube 15 which is arranged below the capillary membrane system 2. The drainage tube has perforations in its walls so that, for example, exudate that has collected in the wound can be suctioned out via the drainage tube, and thus can be removed from the wound. Drainage tube 15 is also routed out of pocket-shaped wound dressing 10 via a correspondingly adapted opening in the top side 11 and can, for example, be connected to a negative pressure unit (not shown).

The invention claimed is:

1. A system for treating wounds using a serum, having a device for recovering serum from whole blood, wherein the device comprises:
a blood bag for receiving whole blood and for coagulating the whole blood into a solid fraction containing the cell components of the blood and a fluid contained in a serum, wherein the blood bag has an outlet for discharging the fluid from the blood bag and a barrier in the region of the outlet that is suitable for retaining at least a majority of the solid fraction,
a filter module that is in fluidic connection with the blood bag via the blood bag outlet,
wherein the filter module has a housing with an interior space and an inner wall that delimits the interior space, in which a semipermeable membrane is arranged that separates the interior space into a retentate space and a permeate space,
wherein the semipermeable membrane enables a separation of the fluid discharged from the blood bag into a permeate that contains the serum and into a retentate in which any particulate components contained in the blood remain, and
wherein the filter module has an inlet device for introducing the fluid discharged from the blood bag into the retentate space, a retentate outlet for discharging the retentate from the retentate space, and a permeate outlet for discharging the permeate from the permeate space, and wherein the system for treating wounds additionally comprises a wound care system for dispensing the permeate onto a wound, which wound care system has a first capillary membrane system with a planar configuration, wherein the first capillary membrane system is connected to at least one supply line so that fluids can be conducted through the supply line and the first capillary membrane system and be delivered to a wound, and wherein the permeate outlet is connected to the first capillary membrane system via a permeate line that includes the at least one supply line of the first capillary membrane system.

2. The system for treating wounds according to claim 1, characterized in that it additionally comprises a second capillary membrane system having a planar configuration that is connected to at least one supply line so that fluids, media, gases and/or other materials can be conducted through the supply line and the second capillary membrane; and a dispenser container which comprises at least one of the supply lines of the second capillary membrane systems is detachably connected to the second capillary membrane system and through which the second capillary membrane system can be supplied with irrigation fluid.

3. The system for treating wounds according to claim 1, characterized in that it comprises a drainage system that can be coupled to a vacuum unit and through which fluids can be withdrawn from the wound to be treated.

4. The system for treating wounds according to claim 1, characterized in that the semipermeable membrane of the filter module is a bundle of hollow-fiber membranes, and the retentate space is formed by the lumina of the hollow-fiber membranes, and the permeate space is formed by the outer space that surrounds the hollow-fiber membranes and is delimited by the interior wall of the housing.

5. The system for treating wounds according claim 4, characterized in that the bundle of hollow-fiber membranes has a U-shaped design.

6. The system for treating wounds according to claim 1, characterized in that the semipermeable membrane of the filter module has a trans-membrane flow ranging from 10,000 to 40,000 l/(m2·h·bar).

7. The system for treating wounds according to claim 1, characterized in that the semipermeable membrane of the filter module has a nominal pore of 0.2 µm.

8. The system for treating wounds according to claim 1, characterized in that the first or the second capillary membrane system is formed in the shape of a mat made from capillary membranes arranged parallel to one another, wherein the capillary membranes are connected to one another in the mat via connecting elements running spaced from one another and parallel to one another, and are maintained at a distance from one another via the connecting elements.

9. The system for treating wounds according to claim 1, characterized in that the capillary membranes of the first or second capillary membrane system are each embedded having at least one of their ends in a respective supply line.

10. The system for treating wounds according to claim 1, characterized in that the first and/or the second capillary membrane system is connected to two respective supply lines, wherein the capillary membranes of the respective capillary membrane system are embedded with their opposite ends in a respective supply line.

11. The system for treating wounds according to claim 1, characterized in that the capillary membranes of the first and/or of the second capillary membrane systems have a trans-membrane flow for water ranging from 0.01 to 50 ml/(min·cm2·bar).

12. The system for treating wounds according to claim 1, characterized in that the capillary membranes of the first and/or of the second capillary membrane systems have a nominal pore of 0.2 µm.

13. The system for treating wounds according to claim 1, characterized in that it additionally comprises a pocket-shaped wound dressing, wherein the pocket-shaped wound dressing is closed on its outer edge and has a top side, a bottom side and a pocket interior, wherein the bottom side and the top side are each formed of a planar material and the bottom side is permeable to fluids, and wherein the first capillary membrane system as well as the possibly present drainage system, as well as any additional capillary membrane systems, if present, are arranged in the pocket interior.

14. The system for treating wounds according to claim 13, characterized in that the bottom side of the pocket-shaped wound dressing is formed from a fleece-like, planar material, or a semipermeable, microporous flat membrane.

15. The system for treating wounds according to claim 1, characterized in that the first and the second capillary membrane systems are identical and form a single supply capillary membrane system that is connected to at least one supply line, and in that the filter module and the dispenser container are connected via at least one supply line of the supply capillary membrane system to the supply capillary membrane system.

* * * * *

UNITED STATES PATENT AND TRADEMARK OFFICE
CERTIFICATE OF CORRECTION

PATENT NO. : 10,617,569 B2
APPLICATION NO. : 15/571407
DATED : April 14, 2020
INVENTOR(S) : Florian Bonn Page 1 of 1

It is certified that error appears in the above-identified patent and that said Letters Patent is hereby corrected as shown below:

In the Specification

Column 1
Line 30, delete "wound" and insert -- wound. --, therefor.

Column 8
Line 61, delete "polytheleneglycol," and insert -- polyethyleneglycol, --, therefor.

In the Claims

Column 16
Line 56, in Claim 5, after "according" insert -- to --.
Line 62, in Claim 6, delete "l/(m2·h·bar)." and insert -- $l/(m^2·h·bar)$. --, therefor.

Column 17
Line 21, in Claim 11, delete "ml/(min·cm2·bar)." and insert -- $ml/(min·cm^2·bar)$. --, therefor.

Signed and Sealed this
Second Day of June, 2020

Andrei Iancu
*Director of the United States Patent and Trademark Office*